United States Patent
Pascali et al.

(10) Patent No.: US 9,005,447 B2
(45) Date of Patent: Apr. 14, 2015

(54) PURIFICATION PROCEDURE FOR THE PREPARATION OF THE RADIOACTIVE TRACER 3'-DEOXY-3'-[$^{18}$F] FLUOROTHYMIDINE ([$^{18}$F]FLT)

(75) Inventors: Claudio Pascali, Rho (IT); Anna Bogni, Barasso (IT)

(73) Assignee: FONDAZIONE IRCCS Istituto Nazionale Dei Tumori, Milan (IT)

( * ) Notice: Subject to any disclaimer, the term of this patent is extended or adjusted under 35 U.S.C. 154(b) by 404 days.

(21) Appl. No.: 12/602,410

(22) PCT Filed: Apr. 22, 2008

(86) PCT No.: PCT/IT2008/000280
§ 371 (c)(1),
(2), (4) Date: May 12, 2010

(87) PCT Pub. No.: WO2008/146316
PCT Pub. Date: Dec. 4, 2008

(65) Prior Publication Data
US 2010/0314322 A1    Dec. 16, 2010

(30) Foreign Application Priority Data

May 29, 2007   (WO) .................. PCT/IT2007/000374

(51) Int. Cl.
*C07B 59/00*   (2006.01)
*C07B 63/00*   (2006.01)
*A61K 51/04*   (2006.01)

(52) U.S. Cl.
CPC ............... *C07B 63/00* (2013.01); *C07B 59/005* (2013.01); *A61K 51/0491* (2013.01)

(58) Field of Classification Search
CPC .. C07B 59/005; A61B 5/02755; G01N 33/60; G01N 33/48; G21H 5/02; A61K 41/00; A61N 5/10; C07H 19/00
See application file for complete search history.

(56) References Cited

FOREIGN PATENT DOCUMENTS

| EP | 2167448 B1 | 8/2011 | |
|---|---|---|---|
| WO | WO 2005/025519 A2 | 3/2005 | |
| WO | WO 2006/133732 A1 | 12/2006 | |
| WO | WO-2006133732 A1 * | 12/2006 | ............... C07B 59/00 |

OTHER PUBLICATIONS

Yun et al., Nuclear Medicine and Biology, 2003, 30, 151-157.*
Fuchtner et al., Appl. Radiat. Isot., 1996, 47(1), pp. 61-66, cited in PTO-892.*
Bio-Rad publication, retrieved on Mar. 23, 2012 from Internet <<http://www.bio-rad.com/webroot/web/pdf/lsr/literature/Bulletin_9119.pdf>>, 7 pages.*
Oh, S. J., Mosdzianowski, C., Chi, D. Y., Kim, J. Y., Kang, S. H., Ryu, J. S., . . . & Moon, D. H. (2004). Fully automated synthesis system of 3'-deoxy-3'-[<sup>18</sup>F] fluorothymidine. Nuclear medicine and biology, 31(6), 803-809.*
Europe, C. (2004). European Pharmacopoeia 5.0.*
Chromafix PS-H+ product information, 2005, retrieved from http://shop.llg.de/info15223_lang_UK.htm on Mar. 10, 2014.*
John R. Grierson and Anthony F. Shields, Radiosynthesis of 3'-Deoxy-3'-[$^{18}$F]fluorothymidine: [$^{18}$F]FLT for Imaging of Cellular Proliferation In Vivo, Nuclear Medicine & Biology, vol. 27, pp. 143-156, 2000.
Mikyung Yun, Seung Jun Oh, Hyun-Joon Ha, Jin Sook Ryu and Dae Hyuk Moon, High radiochemical yield synthesis of 3'-deoxy-3'-[$^{18}$F]fluorothymidine using (5'-*O*-dimethoxytrityl-2'-deoxy-3'-*O*-nosyl-β-D-*threo* pentofuranosyl)thymine and its 3-*N*-BOC-protected analogue as a labeling precursor, Nuclear Medicine and Biology, vol. 30, pp. 151-157, 2003.

* cited by examiner

*Primary Examiner* — Shaojia Anna Jiang
*Assistant Examiner* — Dale R Miller
(74) *Attorney, Agent, or Firm* — Fish & Richardson P.C.

(57) ABSTRACT

A procedure for the preparation of the radioactive tracer 3'-deoxy-3'-[$^{18}$F]fluorothymidine ([$^{18}$F]FLT) comprises the following steps: a) preparation of anhydrous [$^{18}$F]F-fluoride; b) labelling of a precursor, for example 3-N-Boc-1-[5'-O-(4, 4'-dimethoxytrityl)-3'-O-nitrophenylsulfonyl-2'-deoxy-β-D-lyxofuranosyl]thymidine; c) hydrolysis of the mixture obtained by means of the previous steps; d) purification of the mixture to obtain the radioactive tracer [$^{18}$F]FLT. In this procedure steps a), b) and c) are carried out by means of known methods. In step d) the mixture obtained after step c) is purified by means of the passage through a ventilated filter and one or more cartridges of the cationic exchange type (e.g. a Chromafix PS-H+), one or more cartridges of the reversed phase type, and finally a passage through cartridges either of the alumina N type, or diol cartridges, or anionic exchange cartridges or a combination thereof. Furthermore, the mixture which is present in the cartridges is eluted with $H_2O$ for injection, whereby the resulting product is forwarded to a container or ampoule for the collection of [$^{18}$F]FLT.

8 Claims, 2 Drawing Sheets

Fig. 1
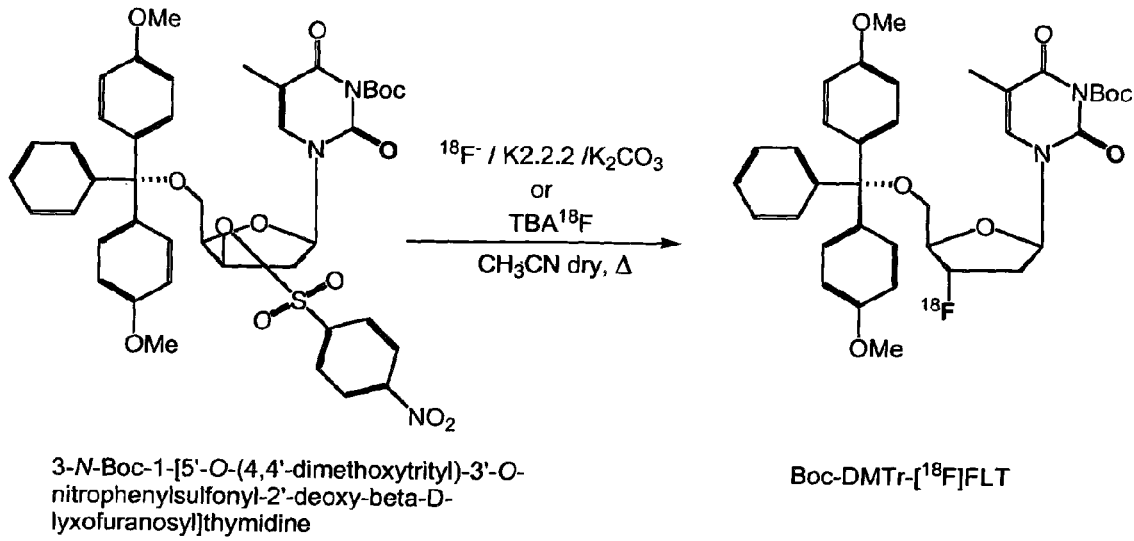
3-N-Boc-1-[5'-O-(4,4'-dimethoxytrityl)-3'-O-nitrophenylsulfonyl-2'-deoxy-beta-D-lyxofuranosyl]thymidine
Boc-DMTr-[$^{18}$F]FLT
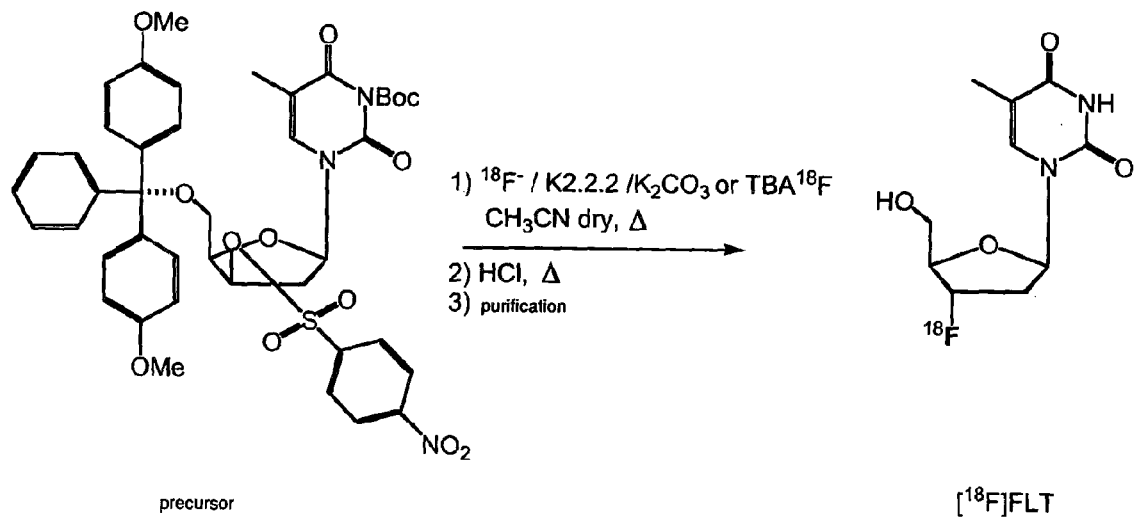
precursor
[$^{18}$F]FLT
Fig. 2

PURIFICATION PROCEDURE FOR THE PREPARATION OF THE RADIOACTIVE TRACER 3'-DEOXY-3'-[$^{18}$F] FLUOROTHYMIDINE ([$^{18}$F]FLT)

RELATED APPLICATION

The present application is a National Phase Application of and claims priority to International Patent Application No. PCT/IT2008/000280 filed on Apr. 22, 2008, which claims priority to International Patent Application No. PCT/IT2007/000374, filed on May 29, 2007, the contents of both of which are incorporated herein by reference.

SUBJECT OF THE INVENTION

This invention refers to the preparation of the radioactive tracer 3'-deoxy-3'-[$^{18}$F] fluorothymidine ([$^{18}$F]FLT). In particular, this invention refers to the preparation of the radioactive tracer 3'-deoxy-3'-[18F] fluorothymidine ([$^{18}$F]FLT) through modules universally known and commonly used for the synthesis of the radioactive tracer [$^{18}$F]FDG which, particularly for this reason, is routinely used in the great majority of positron emission tomography (PET) centres all over the world.

This invention also refers to a kit of reagents/materials for the preparation of the radioactive tracer 3'-deoxy-3'-[$^{18}$F] fluorothymidine ([$^{18}$F]FLT).

BACKGROUND ART

[$^{18}$F]FLT is a radioactive tracer developed in recent years and used in the PET diagnostic procedure in the field of oncology. Its usefulness lies in its ability to differentiate between benign and malignant tissues, in the possibility of measuring the aggressiveness of the tumour and in being able to evaluate the response to antitumoral therapies at an early step.

Despite the considerable interest in this compound, the number of centres equipped to carry out this procedure is extremely limited, as is the number of studies performed on the topic. The reason lies in the current lack of a method of synthesis of [$^{18}$F]FLT extremely simple and effective and, above all, which can be easily automated, unlike the case of the radioactive tracer [$^{18}$F]FDG which, for this and other reasons, is routinely used in most PET centres worldwide.

FIG. 1 shows a known procedure which is used for the preparation of the radioactive tracer 3'-deoxy-3'-[$^{18}$F] fluorothymidine ([$^{18}$F]FLT).

In the case in question, the precursor 3-N-Boc-1-[5-O-(4,4'-dimethoxytrityl)-3-O-nitrophenylsulfonyl-2-deoxy-β-D-lyxofuranosyl] thymidine is used, as recently reported in the literature.

The introduction of [$^{18}$F] fluoride and the subsequent removal of the protective groups with HCl are also well known and commonly used procedures.

The published procedures basically differ in the conditions in which the reactions are carried out (temperature, time, concentration, volume) and in the presence, if any, of an intermediate purification step before the hydrolysis reaction.

The final purification step represents the weak point of these procedures, since HPLC is often used (costly, cumbersome, laborious to manage in routine preparations, more difficult to automate) and must be followed by a "formulation" step (removal of the organic solvent and redissolution of the residue in water or saline solution).

The radiochemical yield is generally low and, more importantly, the end product does not always have the necessary requirements to allow it to be injected in humans. This is due to a number of reasons such as an excessive amount of residual solvents and, if HPLC purification is not carried out, insufficient radiochemical purity and the presence of chemical impurities.

The procedure described in the international patent application no. WO-A-2006/133732 includes an intermediate purification step before hydrolysis, consisting of a hydrolysis reaction on solid support, and an unusual final purification step using disposable commercial columns (commonly called "cartridges" or "SepPaks").

However, it should be pointed out that implementation of this procedure leads to a series of problems such as:
- the automation of the process is laborious and in any case requires a greater number of valves than is normally present on an [$^{18}$F]FDG module;
- there are considerable problems of reproducibility due to obstructions in the tubes caused by partially insoluble compounds;
- significant amounts of "cold" impurities may be present;
- the end product is dissolved in a watery solution containing a percentage of EtOH (15-30%) which is too high for use in humans (the Official Pharmacopoeia states a maximum value of 0.5%); in addition to these limitations, the final radiochemical yield is on average low.

The publication "Radiosynthesis of 3'-deoxy-3'-[$^{18}$F]fluorothymidine: [$^{18}$F]FLT for imaging of cellular proliferation in vivo" Grierson J. R., Shields A. F. Nuclear Medicine Biology 27, 143-156 (2000) describes a relatively complex and laborious procedure which, precisely because of the difficulties that would be caused by its automation, is carried out almost entirely by hand.

This procedure includes the following steps:
a) Preparation of the anhydrous [$^{18}$F]F$^-$ fluoride;
b) Labelling of the precursor;
c) Hydrolysis;
d) Purification.

The result of the procedure is a radiochemical yield of 42% for precursor A and 40% for precursor B, and a radiochemical purity of 97% for precursor A and of 98% for precursor B. Residual solvents can be detected, with a high percentage (15%) of EtOH.

The procedure described in this publication involves a series of problems and disadvantages which limit its use. In particular:
- it requires purification by means of HPLC;
- it cannot be transferred to a normal module for [$^{18}$F]FDG;
- it is not possible to use amounts of precursor greater than 40-45 mg as they spoil the separation by means of HPLC;
- the procedure takes quite a long time to perform.

The main disadvantage, however, is the impossibility of injecting the end product into humans due to the high percentage of EtOH.

The international patent application PCT no. WO 2005/025519 describes a procedure consisting of the following steps:
a) Preparation of the anhydrous [$^{18}$F]F$^-$ fluoride;
b) Labelling of the precursors;
c) Hydrolysis;
d) Purification.

In this last step, a solution of sodium acetate is added to the mixture in the reactor in order to neutralise the pH of the solution. The sodium acetate solution volume is sufficient to dilute the DMSO of the reaction mixture to 1:7.

The diluted and neutralised mixture is transferred to a C18 cartridge on which a frit (2 μm) is placed which makes it possible to block any precipitate that could clog the C18 cartridge. Since the frit can also become clogged once part of the mixture has passed through, a valve was inserted in the setup, making it possible to bypass the frit and to load the remaining mixture directly into the C18 cartridge. This valve is controlled by a line pressure reader which, as the pressure increases (due to clogging) above a certain limit, activates the valve and directs the flow towards the bypass line.

It can be noted that this bypass certainly leads to a considerable loss of activity (and thus of product) on the frit and in the lines that connect the frit to the system as they remain full of reaction, mixture and cannot be washed. In addition, the commercial synthesis modules do not generally foresee this bypass system controlled by a pressure reader. The DMSO, even if greatly diluted, tends to carry the [$^{18}$F]FLT with it which will thus end up in the waste, causing a decrease in the final yield.

The C18 cartridge is then washed with 15.5 mL of water which passes into a waste collection tank. The [$^{18}$F]FLT is then eluted by passing 1 mL of ethanol through the cartridge and into a second container where it is evaporated.

After the ethanol has evaporated, water is added to the reaction mixture which is then transferred to a collection bottle through a cartridge to remove the [$^{18}$F] fluoride and a sterile and apyrogenic filter. It can be noted that the ethanol evaporation step requires a second container that can be heated; this is rarely available in commercial synthesis modules. In addition, the ethanol certainly carries away impurities from the C18 cartridge which are then transferred to the end product.

DESCRIPTION OF THE INVENTION

This invention proposes to overcome the typical problems and disadvantages of the known techniques, and to thus provide a new purification procedure for the production of the radioactive tracer 3'-deoxy-3'-[$^{18}$F]fluorothymidine ([$^{18}$F]FLT), which makes it possible to obtain an end product with a high yield by means of conventional modules and which, above all, can be injected intravenously in humans. This is achieved by means of a procedure with the features described in claim 1. The dependent claims describe particularly advantageous embodiments of the procedure according to this invention.

The procedure according to this invention does not require purification by means of HPLC, which is costly and complex. Nevertheless, the procedure can also be used as a "pre-purification" step if purification with HPLC is preferred. The consequent improvement in terms of chromatographic separation deriving from the reduced amount of loaded material could in this case lead to a considerable improvement in the radiochemical yields reported in the literature.

In addition, the synthesis can be carried out by means of the modules widely used for [$^{18}$F]FDG without any substantial modifications to the hardware. The procedure for preparation of the module before synthesis is also substantially similar to the procedure used for [$^{18}$F]FDG, with the undoubted consequent advantages of daily use.

The procedure according to the invention foresees the use of predetermined types of cartridges for the final purification step; the procedure is also characterised by particular elution methods, which will be described in detail below, and the use of a ventilated filter for loading the final mixture into these cartridges. Furthermore, the materials of the cartridges may be assembled in one single cartridge.

It should also be noted that the procedure according to the invention can be implemented directly or with slight modifications to the existing modules used to produce [$^{18}$F]FDG. It is even possible to use the same module to produce [$^{18}$F]FDG and [$^{18}$F]FLT.

ILLUSTRATION OF DRAWINGS

FIG. 1 shows a procedure for labelling precursor 3-N-Boc-1-[5'-O-(4,4'-dimethoxytrityl)-3'-O-nitrophenylsulfonyl-2'-deoxy-β-D-lyxofuranosyl]thymidine;

FIG. 2 shows another procedure for the synthesis of [$^{18}$F]FLT;

DESCRIPTION OF ONE EMBODIMENT OF THE INVENTION

Figure 3:
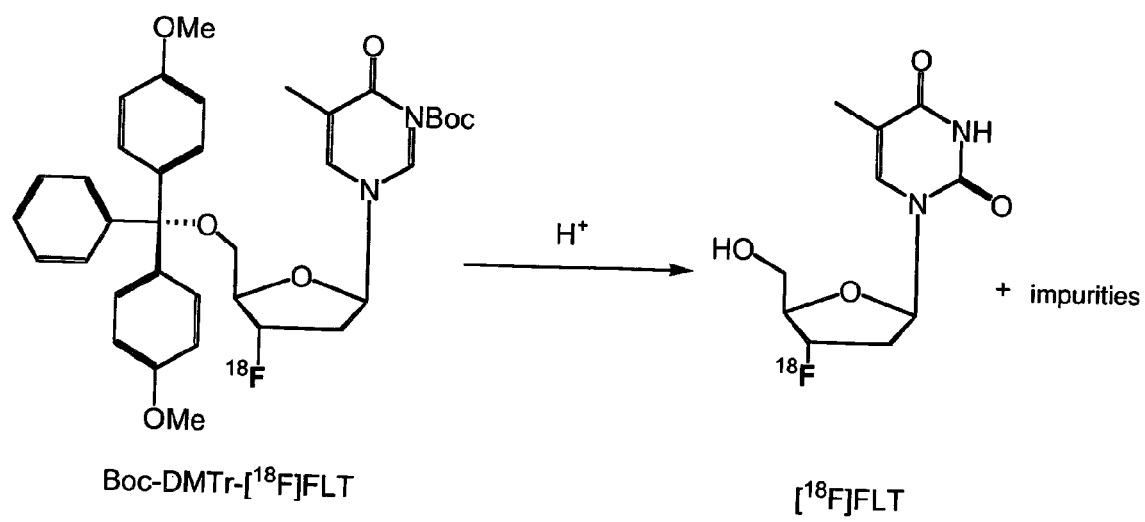
FIG. 3 shows the hydrolysis procedure.

The procedure according to the invention for the synthesis of [$^{18}$F]FLT is described below.

Materials Used.

As stated above, the precursor used in the synthesis is, 3-N-Boc-1-[5'-O-(4,4'-dimethoxytrityl)-3'-O-nitrophenylsulfonyl-2'-deoxy-β-D-lyxofuranosyl]thymidine; however, this precursor has to be considered as a specific example. Operatively, it is possible to use other similar precursors or precursors having a single protective group.

The filters used are 0.22 micron sterile ventilated filters; the filter fitted on the purification column is moistened with H$_2$O immediately before synthesis;

The column for the separation of the anhydrous [$^{18}$F]F$^-$ fluoride is a cartridge with anionic exchange, such as for instance a Chromafix PS-HCO$_3$ cartridge;

The purification is carried out by means of the passage of the final reaction mixture through one or more cartridges with cationic exchange (e.g. a Chromafix PS-H+ cartridge), one or more reverse phase cartridges and finally either an N type alumina cartridge, or a diol cartridge, or a cartridge with anionic exchange or a combination thereof. All the cartridges must be conditioned with 5 mL of EtOH and 5 mL of water for injections.

Synthesis is carried out on a commercial module (such as, for instance, TracerLab Fx) used for the standardised production of [$^{18}$F]FDG, without altering the setup.

Procedure.

According to methods already widely known in the sector, the first step of the procedure consists of preparation of the anhydrous [$^{18}$F]F$^-$ fluoride. This step is well known to the experts and will not therefore be described here below.

The second step consists of the labelling of the precursor, generally 3-N-Boc-1-[5'-O-(4,4'-dimethoxytrityl)-3'-O-nitrophenylsulfonyl-2'-deoxy-β-D-lyxofuranosyl]thymidine. This step is illustrated in FIG. 2, and is also well known to the experts and described in detail in the literature, where it is reported in various conditions of concentration, time and temperature. B1

In particular, it is carried out on 5-30 mg of precursor, dissolved in 0.5-2 mL of anhydrous CH$_3$CN. The reaction is carried out at 85 degrees-120 degrees C. for 3-5 min in the closed reactor. Experiments performed by the applicants showed that at reaction temperatures much lower than the one mentioned above the results are unsatisfactory, while higher reaction temperatures (for example up to 165 degrees C.) increase the risk of breakage due to failure of the valves mounted on the synthesis module and of other components made from plastic.

The third step consists of hydrolysis and is illustrated schematically in FIG. 3. The mixture is cooled at around 60 degrees-80 degrees C. and, if necessary, partially evaporated. HCl 0.8-1N (1-3 inL) is then added and the mixture is heated in the closed reactor for 2-5 min at 75 degrees-105 degrees C. The presence of $CH_3CN$ assists the hydrolysis reaction.

The fourth step represents the main part of the procedure according to the invention. The reaction mixture is partially evaporated at 65 degrees-85 degrees C. with flow-vacuum to reduce the content of $CH_3CN$ to just a few μL as its presence would interfere with the subsequent purification step. After further cooling at 45-50 degrees C. the mixture is purified by means of the passage through one or more cartridges with cationic exchange (e.g. a Chromafix PS-H+ cartridge), one or more reverse phase cartridges and finally a passage through either alumina N cartridges, or diol cartridges, or cartridges with anionic exchange or a combination thereof. Before starting the synthesis, the column is conditioned with EtOH and $H_2O$ for injections and left full of water.

It should be noted that the ventilated filter makes it possible to load the column in the correct way, eliminating the possibility of air entering the column which would make the reproduction of the separation difficult. This is in fact one of the essential points for the success of the method according to the invention.

In fact, even if already mentioned in the literature regarding loading of the reaction mixture in HPLC, this is the first time, to the knowledge of the applicants, that this type of filter has been used for loading the mixture into cartridges.

Tests have also shown that it is essential that the cartridges with cationic exchange are positioned before the other types.

If the reactor is a large size or if the volume of HCl used is small, the reactor can be washed with 1 mL of water and this can then be transferred to the column so as to recover more product.

The cartridges are then eluted with $H_2O$ for injections. The first part is transferred to a container for waste in order to remove part of the impurities and the remaining $CH_3CN$; the second part is transferred to a sterile apyrogenic vial equipped with a vent needle with a 0.22 [mu]m sterile filter at the tip, to collect the [$^{18}$F]FLT. The entry route into the ampoule is preceded by a 0.22 μm sterile filter.

It should be noted that the volumes of $H_2O$ for the elution steps (indicatively 16 mL and 15 mL, respectively) can vary considerably according to the type of C18 cartridge used and the radiochemical yield and level of purity required. It is obvious that if a lower level of purity is accepted then it is possible to increase the amount of [$^{18}$F]FLT.

The choice of cartridge type was dictated by the size and features of those available on the market, the aim being to allow effective purification with as little eluent as possible.

Result

Radiochemical yield: 25-45% corrected for decay.

Total synthesis time: 38-41 min

Radiochemical purity: >98%

Residual solvents: considerably lower than the limits set by the Official Pharmacopoeia for human use.

The procedure according to this invention makes it possible to achieve a series of important advantages with respect to other known procedures for obtaining the radioactive tracer [$^{18}$F]FLT.

In particular:

the procedure does not require purification by means of HPLC, which is costly and complex. Furthermore, other known procedures produce a final product contaminated by large radioactive and nonradioactive impurities;

synthesis can be carried out with the commonly used modules for [$^{18}$F]FDG without the need for substantial changes to the hardware. The procedure for preparation of the module before synthesis is also substantially the same as the method used for [$^{18}$F]FDG, with the undoubted consequent advantages of daily use. Known procedures, on the other hand, can never be adapted to the normally available modules for the production of [$^{18}$F]FDG, which would require considerable modification for adaptation to the production of [$^{18}$F]FLT;

the results obtained are highly reproducible and reliable, unlike those obtained with the procedures known to background art;

the procedure can be used as a "pre-purification" step if purification with HPLC is preferred. The consequent improvement in terms of chromatographic separation as a result of the reduced amount of loaded material would in this case lead to a considerable improvement in the radiochemical yields reported in the literature;

formulated in this way, the product is suitable for intravenous injections in humans, unlike the product obtained by means of the known procedures which is distinguished by its high content of EtOH, making it unsuitable for injections in humans;

the procedure according to this invention does not require final purification with HPLC, which is on the other hand a necessary requirement for the production of [$^{18}$F]FLT by means of known procedures.

The invention is described above with reference to a preferred embodiment, and it has been demonstrated that the procedure according to the invention presents a number of undeniable advantages with respect to the known procedures. The advantages described above confirm the possibility of immediate commercial use of the end product of the procedure according to the invention. In fact, taking into account the considerable increase in production capacity of [$^{18}$F]FLT with limited costs and the fact that the radioactive tracer obtained can be directly injected intravenously into humans, it is possible to provide a kit for the automatic implementation of the procedure, allowing worldwide circulation and use of the end product.

The invention claimed is:

1. A procedure for the preparation of purified radioactive tracer 3'-deoxy-3'-18[F]fluorothymidine ([$^{18}$F]FLT), comprising the following steps:
   a) preparing anhydrous [$^{18}$F]F$^-$ fluoride;
   b) labeling a precursor with the anhydrous [$^{18}$F]F$^-$ to yield a precursor mixture comprising a labelled precursor;
   c) adding HCl to the precursor mixture to achieve hydrolysis of the labelled precursor, thereby yielding a product mixture comprising [$^{18}$F]FLT; and
   d) purifying the product mixture to obtain the purified radioactive tracer [$^{18}$F]FLT, wherein the product mixture is purified by:
   1) passing the product mixture through a ventilated filter to yield a filtrate,
   2) passing the filtrate through one or more cartridges of the cationic exchange type to yield a first eluate,
   3) passing the first eluate through one or more cartridges of the reverse phase type to yield a second eluate, and
   4) passing the second eluate through a cartridge of the alumina N type to yield the purified radioactive tracer [$^{18}$F]FLT,
   wherein the first eluate, the second eluate, and the purified radioactive tracer [$^{18}$F]FLT are eluted with $H_2O$ only for injection, and whereby the purified radioactive tracer [$^{18}$F]FLT is forwarded to a container or ampoule for collection, and wherein the radiochemical purity of the purified radioactive tracer [$^{18}$F]FLT exceeds 98% and the percentage of residual solvents in the purified radioactive tracer [$^{18}$F]FLT is less than 0.5%.

2. The procedure according to claim 1, wherein the precursor is 3-N-Boc-I-[5'-O-(4,4'-dimethoxytrityl)-3'-O-nitrophenylsulfonyl-2'-deoxy-β-D-[lyxofuranosyl]thymidine.

3. The method of claim 1, wherein purifying the product mixture does not include purifying via HPLC.

4. The method of claim 1, wherein the radiochemical yield of the purified radioactive tracer [$^{18}$F]FLT is 25-45%.

5. The method of claim 1, wherein the total synthesis time is about 40 minutes.

6. The method of claim 1, wherein the purified radioactive tracer [$^{18}$F]FLT is suitable for intravenous injection into humans.

7. The method of claim 1, further comprising conditioning the one or more cationic exchange type cartridges, the one or more reverse phase type cartridges, and the alumina N type cartridge with H$_2$O and EtOH before purifying the product mixture.

8. The method of claim 7, further comprising filling the one or more cationic exchange type cartridges, the one or more reverse phase type cartridges, and the alumina N type cartridge with H$_2$O after conditioning the cartridges and before purifying the product mixture.

\* \* \* \* \*